United States Patent [19]
Yamaguchi et al.

[11] Patent Number: 5,942,754
[45] Date of Patent: *Aug. 24, 1999

[54] METHOD OF AND APPARATUS FOR DETERMINING HYDROGEN PEROXIDE

[75] Inventors: Yoshinori Yamaguchi; Masayuki Yagi; Dou Xiaoming; Emi Ashibe; Harumi Uenoyama, all of Kyoto, Japan

[73] Assignee: Kyoto Dai Ichi Kagaku Co., Ltd., Kyoto, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/562,814

[22] Filed: Nov. 27, 1995

[30] Foreign Application Priority Data

Nov. 25, 1994 [JP] Japan ................................. 6-315933
Nov. 25, 1994 [JP] Japan ................................. 6-315934

[51] Int. Cl.[6] ................................................. G01N 21/35
[52] U.S. Cl. .............................. 250/339.12; 250/339.11; 250/341.8; 250/343
[58] Field of Search ..................... 250/339.12, 339.11, 250/341.8, 343

[56] References Cited

U.S. PATENT DOCUMENTS

| | | | |
|---|---|---|---|
| 3,591,287 | 7/1971 | Hannis | 356/51 |
| 3,654,179 | 4/1972 | Baher et al. | 252/408 |
| 4,169,676 | 10/1979 | Kaiser | 356/39 |
| 4,595,833 | 6/1986 | Sting | 250/339.11 |
| 4,800,279 | 1/1989 | Hieftj et al. | 250/339.12 |
| 5,097,130 | 3/1992 | Koashi et al. | 250/339.12 |
| 5,121,337 | 6/1992 | Brown | 250/339.12 |
| 5,137,023 | 8/1992 | Mendelson et al. | 128/633 |
| 5,250,811 | 10/1993 | Lippert et al. | 250/339.11 |
| 5,349,188 | 9/1994 | Maggard | 250/339.12 |
| 5,362,445 | 11/1994 | Miyahara et al. | 422/82.09 |
| 5,412,581 | 5/1995 | Tacket | 250/339.12 |
| 5,434,411 | 7/1995 | Miyahara et al. | 250/339.11 |
| 5,506,110 | 4/1996 | Matsuura et al. | 435/7.94 |
| 5,607,643 | 3/1997 | Xiaoming et al. | 422/82.05 |

FOREIGN PATENT DOCUMENTS

| | | | |
|---|---|---|---|
| 0 124 287 A3 | 11/1984 | European Pat. Off. | |
| 61-281946 | 12/1986 | Japan | 250/339.11 |
| WO 90/11510 | 10/1990 | WIPO | |

OTHER PUBLICATIONS

Guiguere, Paul A. The Infra–red Spectrum of Hydrogen Peroxide, The Journal odf Chemical Physics vol. 18, No. 1, pp. 88–92, Jan. 1950.

Abstract of Japanese Patent Publ. No. JP60218069, dated Oct. 31, 1985.

Abstract of Japanese Patent Publ. No. JP60060729, dated Apr. 8, 1985.

*Primary Examiner*—Constantine Hannaher
*Attorney, Agent, or Firm*—Nikaido Marmelstein Murray & Oram LLP

[57] ABSTRACT

A sample solution is stored in a total reflection cell, and a measuring beam is introduced from an incident optical system to be totally reflected, for measuring a total reflection absorption spectrum. Hydrogen peroxide contained in the sample solution is determined on the basis of absorbance at the position of any absorption peak of the spectrum which is present at 1200 to 1500 $cm^{-1}$ or 2600 to 3000 $cm^{-1}$. Hydrogen peroxide contained in an aqueous solution can be simply quantitatively analyzed through optical analysis.

19 Claims, 21 Drawing Sheets

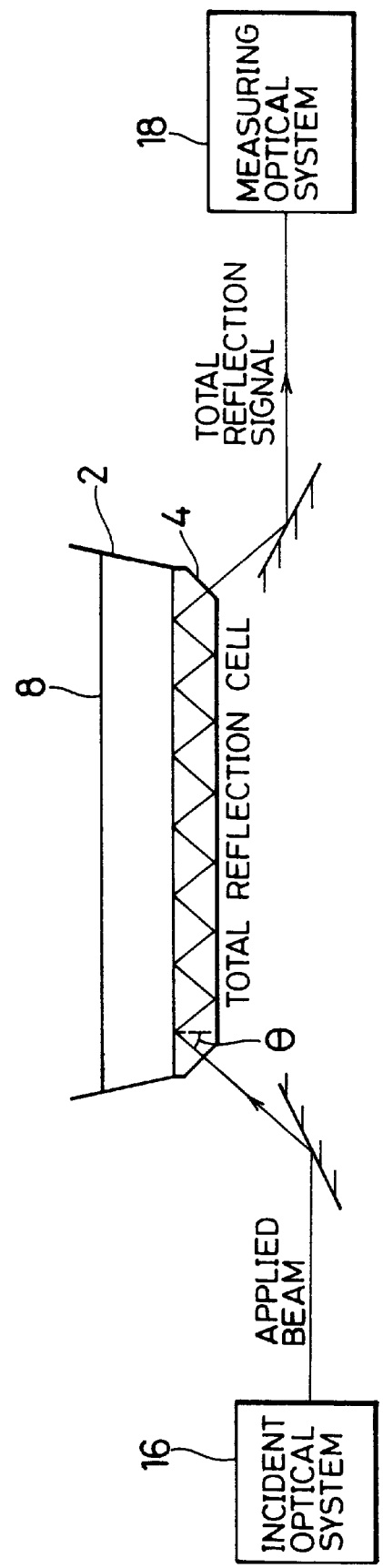

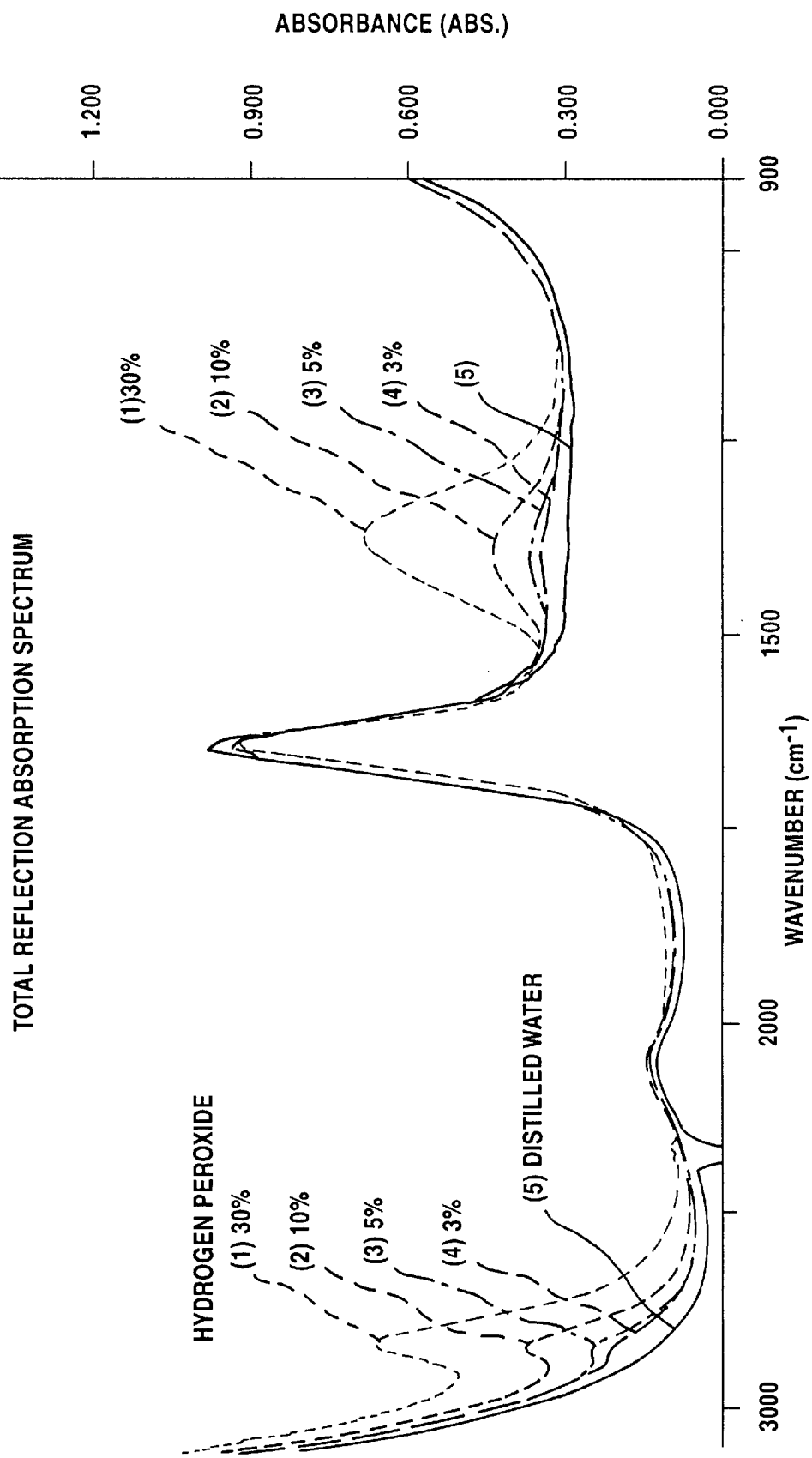

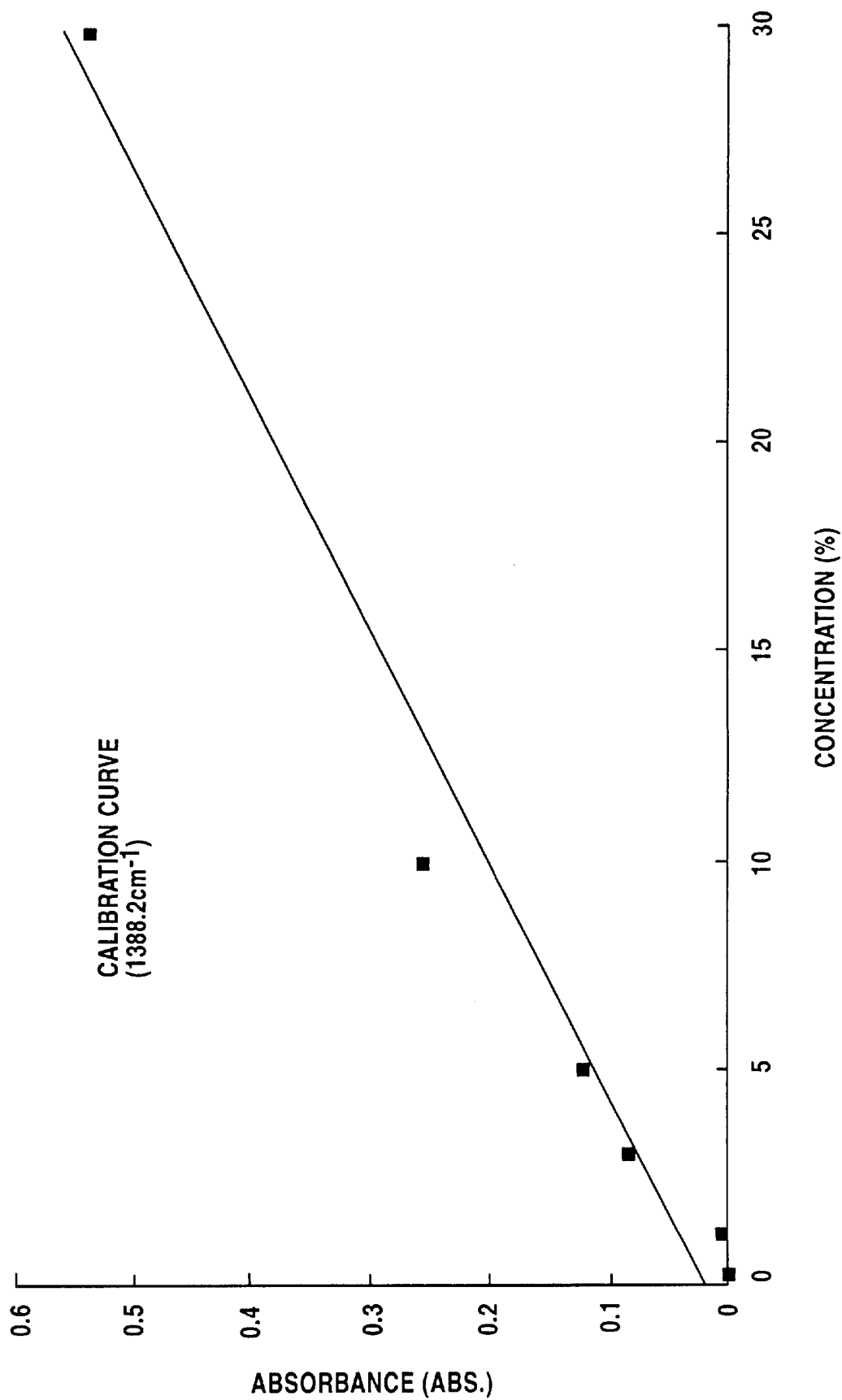

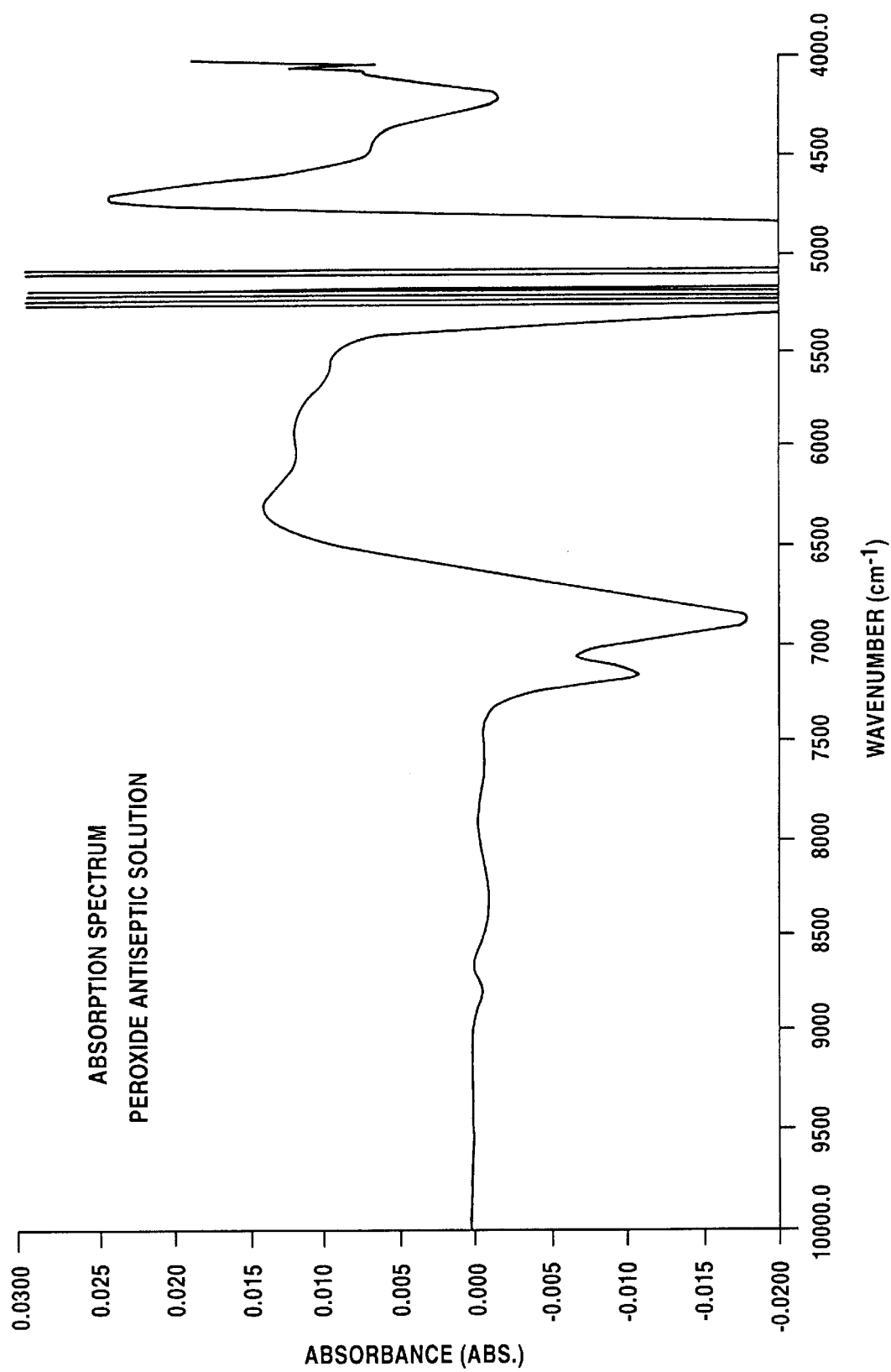

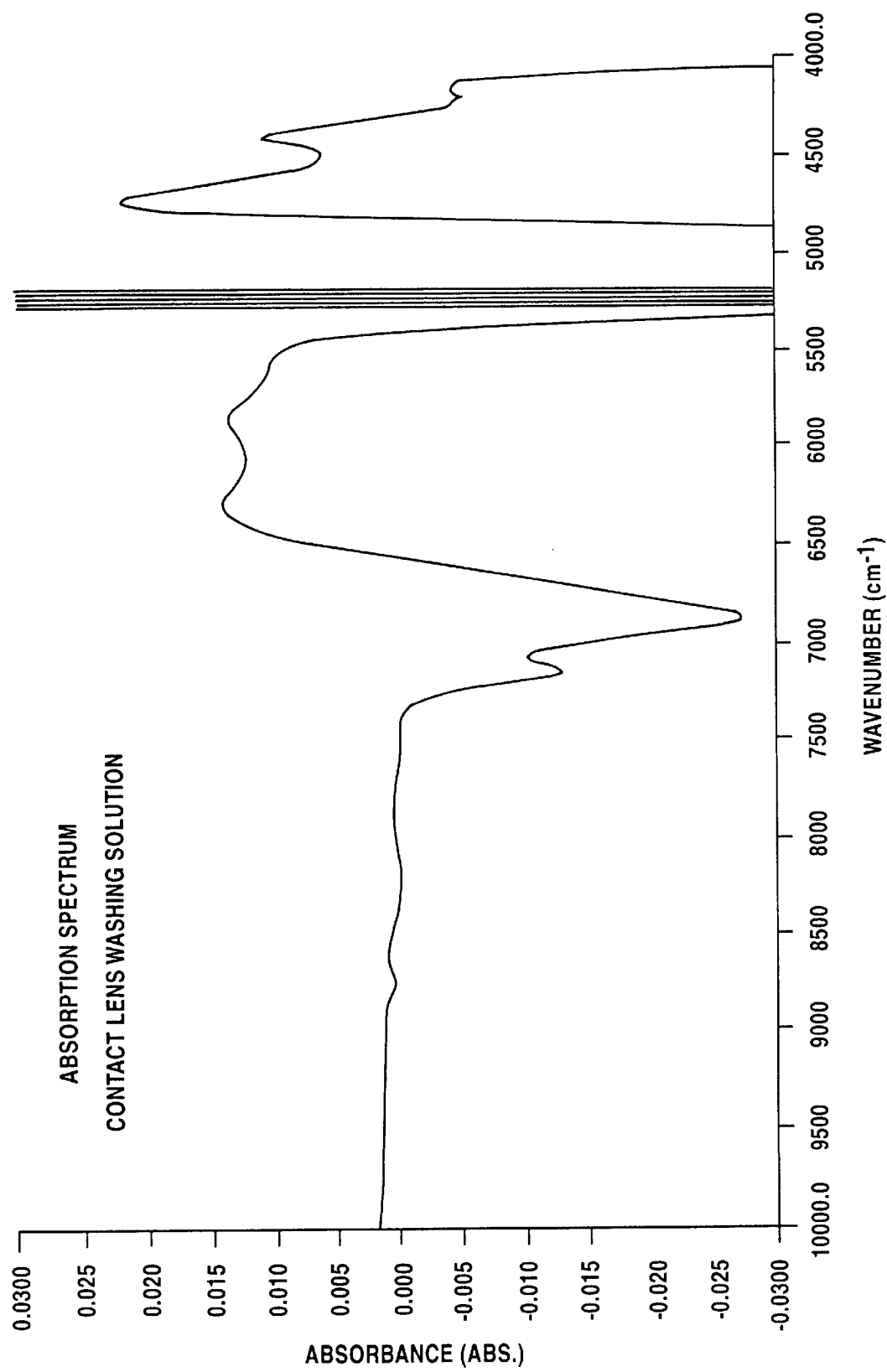
Fig.21 ABSORPTION SPECTRUM
CONTACT LENS WASHING SOLUTION

METHOD OF AND APPARATUS FOR
DETERMINING HYDROGEN PEROXIDE

BACKGROUND OF THE INVENTION

1. Field of the Invention

The present invention relates to a method of determining hydrogen peroxide for quality-controlling a commercially available aqueous solution containing hydrogen peroxide or another substance containing hydrogen peroxide, or in a hydrogen peroxide formation or decomposition system in chemical reaction such as enzyme reaction, and an apparatus which is employed therefor.

2. Description of the Background Art

In relation to determination of hydrogen peroxide in an aqueous solution, the following methods are known in the art:

(1) A method employing a hydrogen peroxide electrode.
(2) Leuco or oxidation condensation type spectrophotometry (refer to Japanese Patent Laying-Open Gazette No. 59-182361 (1984)), which is typically adapted to react hydrogen peroxide with 4-aminoantipyrin and phenol for coloring, and to measure absorption of the coloring reaction solution at 505 nm.
(3) A fluorescent method, which is adapted to react hydrogen peroxide with homovanillic acid to generate fluorescence, and to measure the fluorescence.
(4) Chemiluminescence, which is adapted to excite a substrate of luminol or lucigenin through oxidizing power of hydrogen peroxide under presence of a catalyst such as POD (peroxidase) and to detect light generated when the substrate returns from the excited state to the ground state.

The aforementioned methods (1) to (4) of determining hydrogen peroxide in aqueous solution samples have the following problems:

The method (1) is adapted to measure current change which is caused when hydrogen peroxide is electrically oxidized, and hence an influence is exerted by a reducing substance coexisting in the sample solution.

In the leuco type spectrophotometry (2), an error is readily caused by coloring of a reagent blank resulting from natural oxidation of a chromogen. In the oxidation condensation type spectrophotometry (2), on the other hand, a negative error is readily caused by a reducing substance. Further, hydrogen oxide of 2 moles is required for forming a pigment of 1 mole, and hence this method is unsuitable for determination of a component of a small quantity.

In the fluorescent method (3), sensitivity remarkably depends on the performance of an apparatus. Thus, this method is extremely influenced by a temperature and a coexistent substance.

In the chemiluminescence (4), a sufficient quantity of light emission is obtained only under alkaline conditions. The reaction rate is slow and reproducibility is insufficient. Further, light emission intensity is reduced upon coexistence of protein.

SUMMARY OF THE INVENTION

An object of the present invention is to enable simple quantitative analysis of hydrogen peroxide in an aqueous solution through optical analysis means.

According to the present invention, hydrogen peroxide is determined through absorption of hydrogen peroxide in an aqueous solution over infrared and near infrared regions.

In a first method of the present invention employing absorption in the infrared region, a sample solution is in existence in a cell having a total reflection prism at least on one surface thereof, a measuring beam including light in the infrared region is introduced into the total reflection prism to be totally reflected, and absorbance at any one absorption peak which is present at 1200 to 1500 $cm^{-1}$ or 2600 to 3000 $cm^{-1}$ in absorption of the measuring beam caused in the interface between the total reflection prism and the sample solution is measured, thereby determining hydrogen peroxide. The absorbance in total reflection is measured from intensity of attenuated total reflection.

A hydrogen peroxide determination apparatus which is applied to the first method of the present invention making measurement in the infrared region comprises a total reflection cell having a total reflection prism consisting of a material having a larger refractive index than a sample solution on at least one of wall surfaces defining a space storing the sample solution, an incident optical system, including an infrared light source, for introducing a measuring beam of the infrared region into the total reflection prism at an angle of incidence causing total reflection, and a measuring optical system receiving an outgoing beam from the total reflection prism for measuring absorbance of at least one absorption peak which is present at 1200 to 1500 $cm^{-1}$ or 2600 to 3000 $cm^{-1}$.

The light source which is included in the incident optical system is that generating a beam of a continuous wavelength, and a spectroscope is included in the incident optical system or the measuring optical system to make spectral measurement. The measuring beam includes a continuous wavelength beam of a mid infrared region including 1200 to 1500 $cm^{-1}$ and 2600 to 3000 $cm^{-1}$.

FIG. 1 schematically illustrates the first method employing a total reflection cell 2. At least one surface of the total reflection cell 2 is formed by a total internal reflection prism 4. A sample solution 8 is in existence in the total reflection cell 2 and a measuring beam is introduced into the total reflection prism 4 from an incident optical system 16 at an angle θ of incidence for causing total reflection, whereby the measuring beam is transmitted through the total reflection prism 4 while being totally reflected. At this time, the measuring beam slightly permeates toward the sample solution 8 in the interface between the total internal reflection prism 4 and the sample solution 8, and a specific wavelength component of an evanescent wave of excitation energy of the measuring beam is absorbed by hydrogen peroxide. The outgoing beam from the total internal reflection prism 4 is separated into its spectral components by a measuring optical system 18 so that absorbance by total reflection of a characteristic wavelength component thereof is measured, thereby determining hydrogen peroxide in the sample solution.

Assuming that $n_2$ represents the refractive index of a sample solution and $n_1$ ($n_2<n_1$) represents that of a total refection prism, a critical angle θc causing total reflection is expressed as follows:

$$\theta c = \sin^{-1}(n_2/n_1) \text{ (where } 0°<\theta c<90°)$$

The angle θ of incidence upon the interface between the total reflection prism 4 and the sample solution 8 in the case of introducing a measuring beam into the total reflection prism 4 from the incident optical system 16 is set in the following condition:

θ>θc

Absorption in the total reflection prism 4 is expressed by absorbance A as follows:

A=N·a·de·loge where N represents the number of times of total reflection in the total reflection prism 4, a represents the absorption coefficient of the sample solution 8, and de represents the optical path length along which the measuring beam permeates into the sample solution 8 in single total reflection.

In a second method of the present invention employing absorption in the near infrared region, on the other hand, a measuring beam including light of the near infrared region is introduced into a sample solution which is in existence in a light-transmittable cell, and hydrogen peroxide is determined on the basis of absorbance of any absorption peak which is present at 4300 to 4800 cm$^{-1}$ or 5400 to 6600 cm$^1$ in the transmitted light.

A hydrogen peroxide determination/measuring apparatus which is applied to the second method of the present invention for making measurement in the near infrared region employs a light-transmittable cell, in place of the total reflection cell in the measuring apparatus for the first method.

The method according to the present invention can be applied not only to measurement of an aqueous solution sample already containing hydrogen peroxide, but to monitoring of a reaction system such as enzyme reaction of forming or decomposing hydrogen peroxide.

In a first example, the method according to the present invention is applied to a reaction system of forming hydrogen peroxide by specific reaction between an oxidizing enzyme and a biological or metabolic component. Assuming that S represents a substrate, P represents a product and E represents an enzyme, the quantity of hydrogen peroxide which is formed by the following reaction is measured by the method according to the present invention. The quantity of the substrate S or the product P can be obtained from the measured quantity of hydrogen peroxide. Further, enzyme activity can also be measured from the measured quantity of hydrogen peroxide.

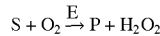

Exemplary combinations of the substrate S and the enzyme E are glucose and glucose oxidase, cholesterol and cholesterol oxidase, urea and uricase, pyruvic acid and oxidase pyruvate, and hexose and pyranose oxidase, while the combination is not restricted to these so far as enzyme reaction of forming hydrogen peroxide is caused.

A second example is adapted to make reaction through an enzyme which is specifically reacted with hydrogen peroxide and decomposes the same, for measuring hydrogen peroxide by the method according to the present invention. Assuming that $PH_2$ represents a reactant, P represents a product and E represents an enzyme, the quantity of the reactant $PH_2$ or the product P can be obtained by measuring the quantity of reduced hydrogen peroxide by the following enzyme reaction. Further, enzyme activity can also be measured by the measured quantity of reduced hydrogen peroxide.

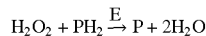

While the enzyme can be a dehydrogenase such as peroxidase or catalase, the present invention is also applicable to reaction which is related to another enzyme so far as the same is conjugate reaction with hydrogen peroxide.

It is possible to first label a reactant with a compound such as peroxidase or catalase having reactivity with hydrogen peroxide and to thereafter react the reactant with a constant quantity of hydrogen peroxide, thereby estimating the quantity of the reactant from that of reduced hydrogen peroxide. For example, the quantity of an antibody is measured by reacting an anti-antibody, which is labelled with peroxidase, with an antigen-antibody reaction combination, performing BF separation of separating and removing the unreacted labelled anti-antibody from that reacted with the antigen-antibody reaction combination, and thereafter reacting peroxidase with hydrogen peroxide, for measuring the quantity of reduced hydrogen peroxide. Either the antigen or the antibody, or either the antibody or the anti-antibody may be labelled. The antigen-antibody reaction is well known to those skilled in the art, and a method of making the antigen-antibody reaction is not limited.

According to the present invention, hydrogen peroxide concentration can be determined on the basis of intensity of the peak of the Raman shift wavenumber of 800 to 920 cm$^{-1}$ by irradiating the sample solution with the exciting beam and detecting Raman scattering light, whereby hydrogen peroxide can be directly determined with no requirement for a secondary operation such as reaction of a light emitting substance through reducing or oxidizing power of hydrogen peroxide dissimilarly to the prior art, and hence errors following the reaction are reduced.

Most enzyme reaction generates hydrogen peroxide. While enzyme reaction is generally monitored with a color former, the enzyme reaction can be directly monitored by the inventive method with no employment of a color former.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 5 illustrates total reflection absorption spectra of hydrogen peroxide standard samples of some concentration levels and distilled water;

FIG. 6 illustrates a hydrogen peroxide calibration curve based on absorbance values at the peak position of an absorption wavenumber of 1388.2 cm$^{-1}$ in the total reflection absorption spectra shown in FIG. 5;

FIG. 20 illustrates a near infrared absorption spectrum of a commercially available peroxide antiseptic solution; and FIG. 21 illustrates a near infrared absorption spectrum of a commercially available contact lens washing solution.

DESCRIPTION OF THE PREFERRED EMBODIMENTS

Figure 2:
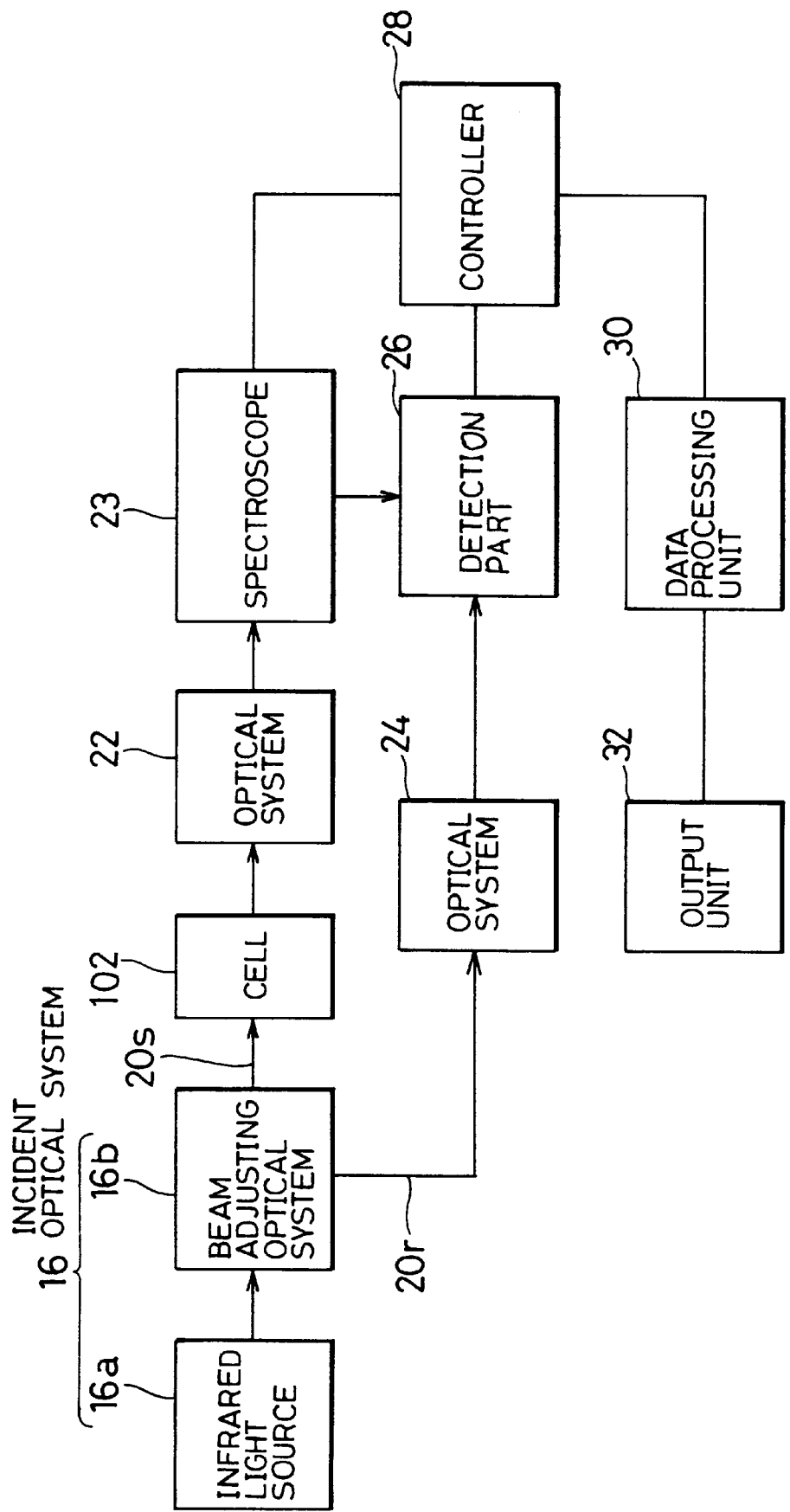
FIG. 2 is a block diagram schematically showing a measuring apparatus according to an embodiment of the present invention.

FIG. 2 schematically illustrates a measuring apparatus according to an embodiment of the present invention. A measuring cell 102 is formed by a total reflection cell for measuring absorption in the infrared region, or by a light-transmittable cell for measuring absorption in the near infrared region.

The total reflection cell has a total reflection prism on at least one surface thereof. This total reflection cell can be formed by a cell having only one opening for receiving a sample solution, or a flow cell, having an inlet port and an outlet port, which is fed with the sample solution. The material for the total internal reflection prism can be prepared from ZnSe, Ge, Si, Al$_2$O$_3$ or MgO. This material may be employed for only the total reflection cell, or for all wall surfaces of the total reflection cell including the total internal reflection prism.

On the other hand, the light-transmittable cell is made of a material such as glass, quartz or polyethylene terephthalate, for receiving or passing the sample solution.

An incident optical system 16 includes an infrared light source 16a generating a measuring beam and a beam adjusting optical system 16b. The light source 16a generates a beam including a continuous wavelength beam. A fluorescent lamp, a xenon lamp or a black body radiation source can be employed for infrared light. On the other hand, a halogen lamp, a fluorescent lamp, a xenon lamp or a black-body radiation source can be employed for near infrared light. That generating a wide wavelength beam over the infrared and near infrared regions can be applied to measurement in both regions in common.

The beam adjusting optical system 16b includes an optical system for converting the beam from the light source 16a into a parallel beam, a beam splitter for separating the same into a measuring beam 20s and a reference beam 20r, and an optical system for introducing the measuring beam 20s into the measuring cell 102. In the case that the measuring cell 102 is formed by a total reflection cell, the beam adjusting optical system 16b is so adjusted as to introduce the beam into the total reflection prism at an angle of incidence causing total reflection.

An optical system 22 for adjusting a luminous flux of the measuring beam 20s totally reflected by and transmitted through the total reflection prism or that transmitted through the light-transmittable cell, and a spectroscope 23 such as an FTIR (Fourier transformation infrared spectrophotometer) for receiving the measuring beam 20s which is adjusted by the optical system 22 and separating the measuring beam 20s into its spectral parts are arranged on an optical path of the measuring beam 20s, so that the measuring beam 20s which is separated into its spectral parts is guided to and detected by a detection part 26. The measuring optical system 18 in FIG. 1 comprises the optical system 22, the spectroscope 23 and the detection part 26 in FIG. 2.

On the other hand, an optical system 24 for adjusting the luminous flux of the reference beam 20r is arranged on the optical path of the reference beam 20r for correcting fluctuation of the measuring beam 20s, so that the adjusted reference beam 20r is guided to and detected by the detection part 26. The detection part 26 is adapted to correct the measuring beam 20s which is separated into its spectral parts through the measuring cell 102 and the spectroscope 23 with intensity of the reference beam 20r indicating light source intensity for calculating absorbance.

Numeral 28 denotes a controller which controls the spectral operation at the spectroscope 23 and transmits a detection output of the detection part 26 to a data processing unit 30. Numeral 32 denotes an output unit such as a recorder or a CRT outputting a processing result of the data processing unit 30.

FIGS. 3A to 4E illustrate exemplary total reflection cells.

Figure 3A:
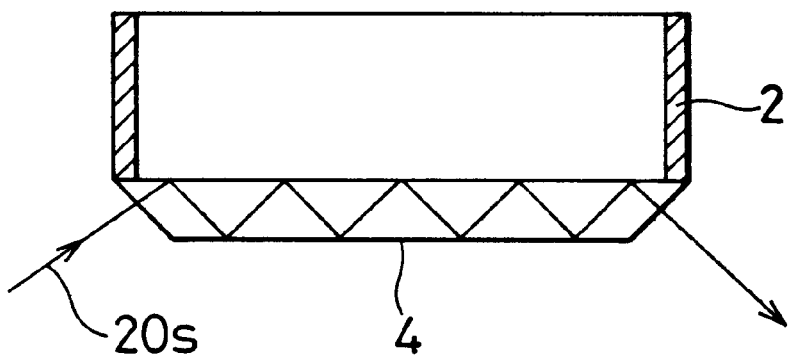
FIG. 3A is a front sectional view showing a first exemplary total reflection cell having only one opening.
Figure 3B:
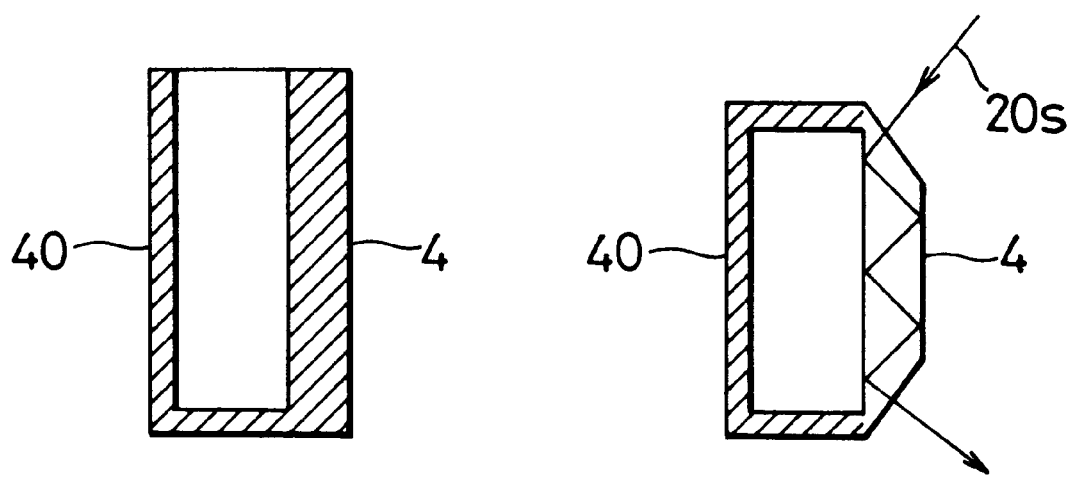
FIG. 3B shows front and top sectional views of a second exemplary total reflection cell having only one opening.

FIGS. 3A and 3B illustrate exemplary reflection cells having only single openings. FIG. 3A shows the cell 2 illustrated in FIG. 1, having a total reflection prism 4 on its bottom surface. FIG. 3B shows front and top sectional views of a cell 40 having a total reflection prism 4 on its side surface respectively. A measuring beam 20s is introduced into the prism 4 in a horizontal plane.

FIGS. 4A to 4E show perspective and front sectional views of cells having other shapes respectively.

Figure 4A:
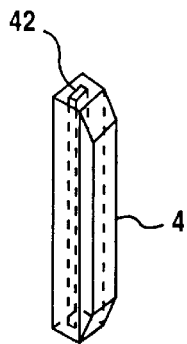
FIG. 4A shows perspective and front sectional views of a throwaway total reflection cell respectively.
Figures 1, 4A:
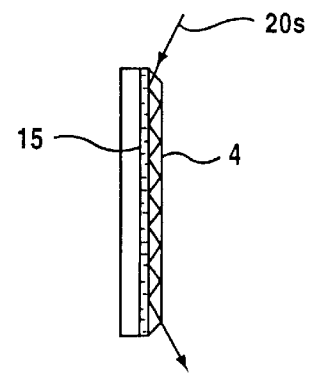
FIG. 1 schematically illustrates a first method of the present invention employing a total reflection cell.

FIG. 4A shows a single-sided throwaway cell, which is provided with a narrow clearance 42 for sucking a sample solution by a capillary phenomenon, and a total internal reflection prism 4 is formed along the clearance 42. Numeral 15 denotes the sample solution which is sucked along the clearance 42.

Figure 4B:
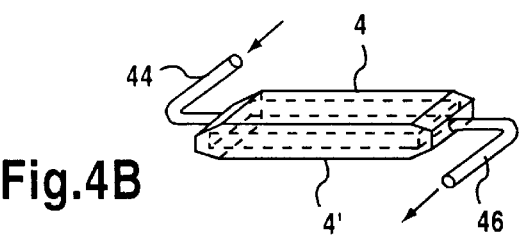
FIGS. 4B to 4E show perspective and front sectional views of exemplary total reflection flow cells respectively.
Figures 1, 4B:
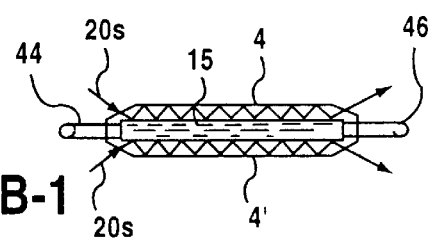

FIG. 4B shows an exemplary double-sided total reflection flow cell, which is provided with total internal reflection prisms 4 and 4' on upper and lower surfaces thereof through a space fed with a sample solution. Numeral 44 denotes an inlet port for introducing the sample solution into the cell, and numeral 46 denotes an outlet port for the sample solution.

Figure 4C:
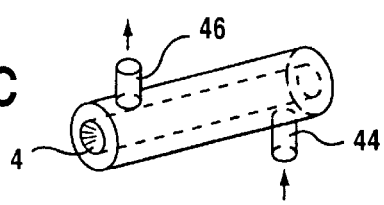
Figures 1, 4C:
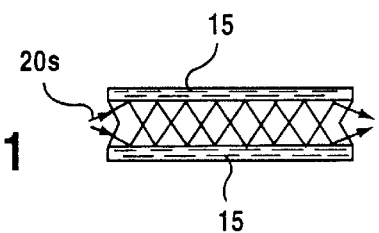

FIG. 4C shows an exemplary cylindrical surface total reflection flow cell, which is formed to enclose a side surface of a cylindrical total reflection prism 4, so that a sample solution 15 is fed along the cylindrical surface of the total reflection prism 4.

Figure 4D:
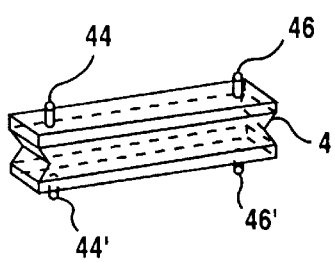
Figures 1, 4D:
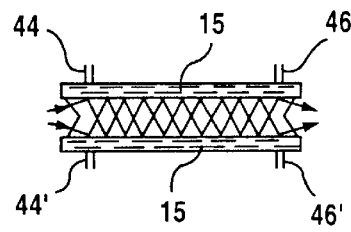

FIG. 4D shows another exemplary double-sided total reflection flow cell, which is so formed that a sample solution 15 flows along two opposite planes of a total reflection prism 4 respectively.

Figure 4E:
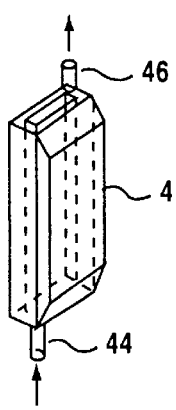
Figures 1, 4E:
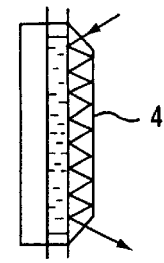

FIG. 4E shows an exemplary single-sided total reflection flow cell, which has a total reflection prism 4 on one surface defining a space fed with a sample solution 15.

EXAMPLE 1

Example of making measurement with a total reflection cell comprising a total reflection prism of a ZnSe crystal is now described.

(Formation of Calibration Curve)

A standard hydrogen peroxide reagent of 30% (Lot 3018930428 by Santoku Chemical Industries Co., Ltd.) was diluted with distilled water to prepare hydrogen peroxide standard samples of 10%, 5%, 3% and 1% respectively, and total reflection absorption spectra of these standard samples and water were measured. FIG. 5 shows the results. The spectrum of the standard sample of 1% is omitted since the same is approximate to that of the distilled water. Absorption peaks of hydrogen peroxide are observed at positions of wavenumbers 1388.2 $cm^{-1}$ and 2831.9 $cm^{-1}$ respectively.

FIG. 6 shows a hydrogen peroxide calibration curve formed by plotting the absorbance values at the peak position of 1388.2 $cm^{-1}$ in the spectra shown in FIG. 5 on the axis of ordinates while plotting concentration values on the axis of abscissas.

Figure 7:
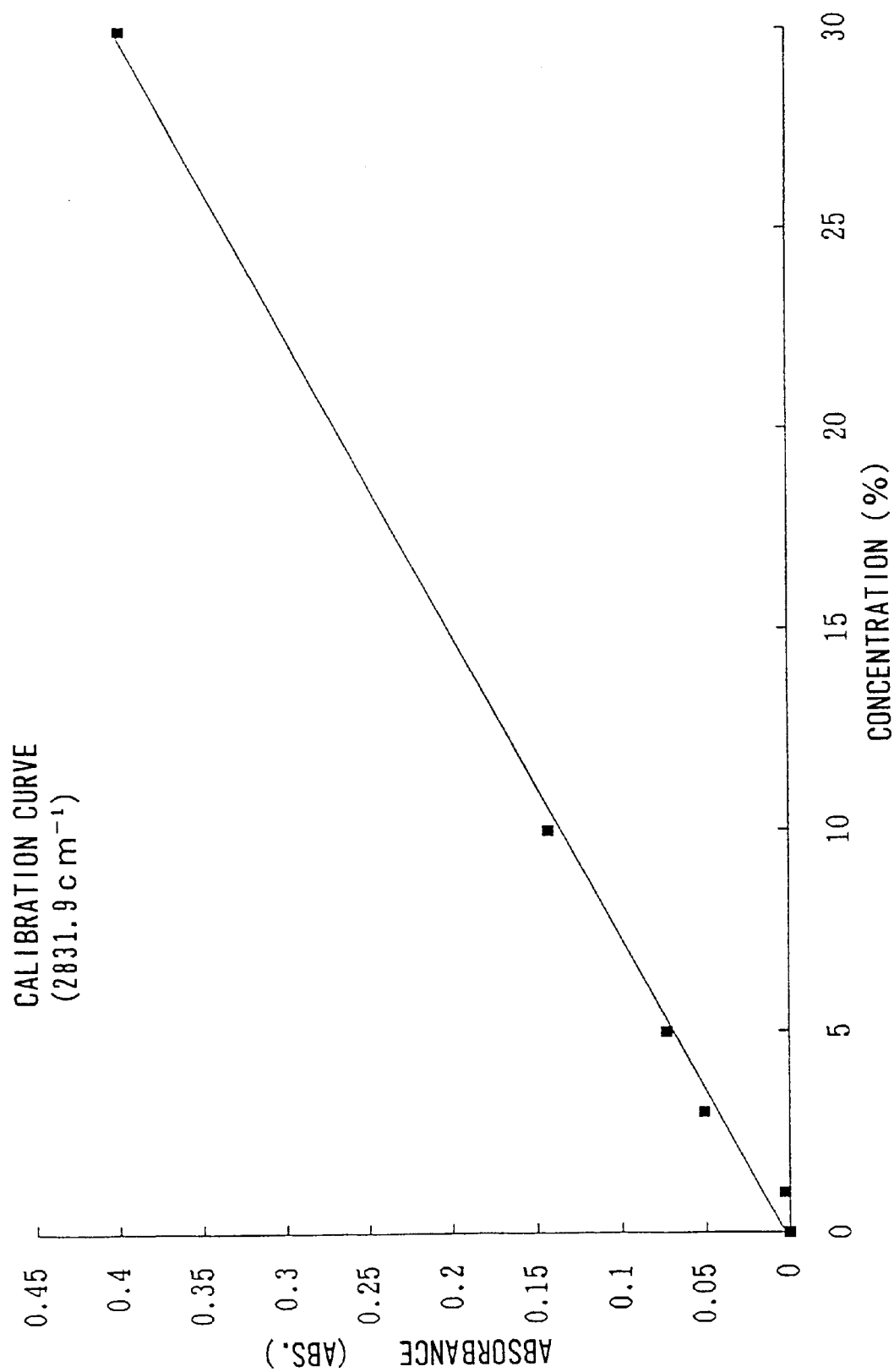
FIG. 7 illustrates a hydrogen peroxide calibration curve based on absorbance values at the peak position of an absorption wavenumber of 2831.9 cm$^{-1}$ in the total reflection absorption spectra shown in FIG. 5.

FIG. 7 shows a hydrogen peroxide calibration curve formed by plotting the absorbance values at the peak position of 2831.9 $cm^{-1}$ in the spectra shown in FIG. 5 on the axis of ordinates while plotting concentration values on the axis of abscissas.

(Sample Measurement)

Examples of determining commercially available hydrogen peroxide solutions with these calibration curves are now described.

Figure 8:
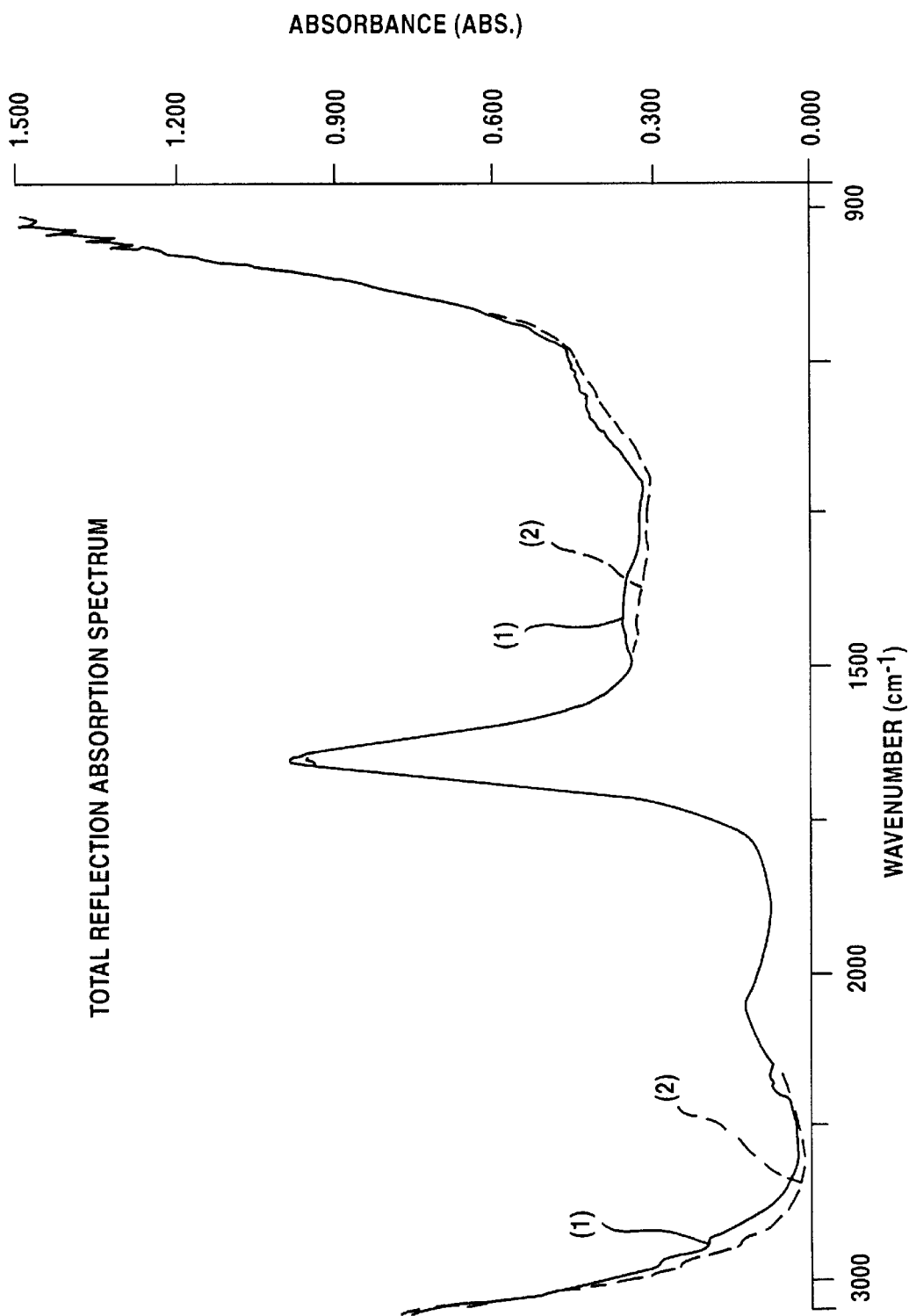
FIG. 8 illustrates total reflection absorption spectra of a commercially available contact lens washing solution and distilled water.

(1) Measurement of Commercially Available Contact Lens Washing Solution:

Similarly to the measurement for formation of the calibration curves, a commercially available contact lens washing solution (Consent F (trade name) imported by Barndshaind Co., Ltd.) (calculated as 2.98% from indicated concentration) was measured to obtain a total reflection absorption spectrum ① in FIG. 8. ② shows a total reflection absorption spectrum of distilled water which was measured in a similar manner.

Figure 9:
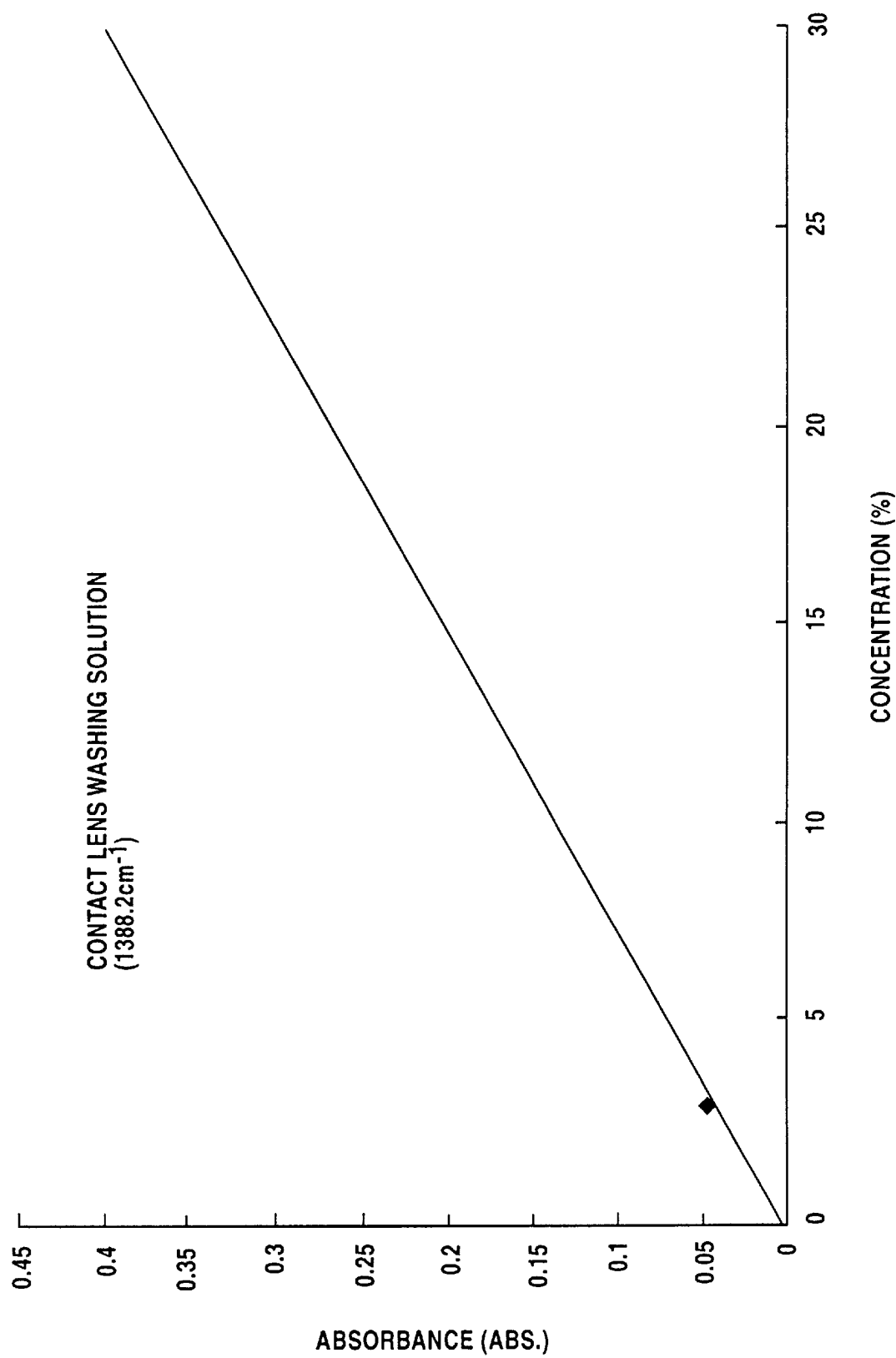
FIG. 9 illustrates the absorbance values at the peak position of 1388.2 cm$^{-1}$ in the total reflection absorption spectra shown in FIG. 8, which are applied to the calibration curve of FIG. 6.

Absorbance of the spectrum at a peak position of 1388.2$cm^{-1}$ was calculated and applied to the calibration curve of FIG. 6, thereby estimating hydrogen peroxide concentration of 3.11%, as shown in FIG. 9.

Figure 10:
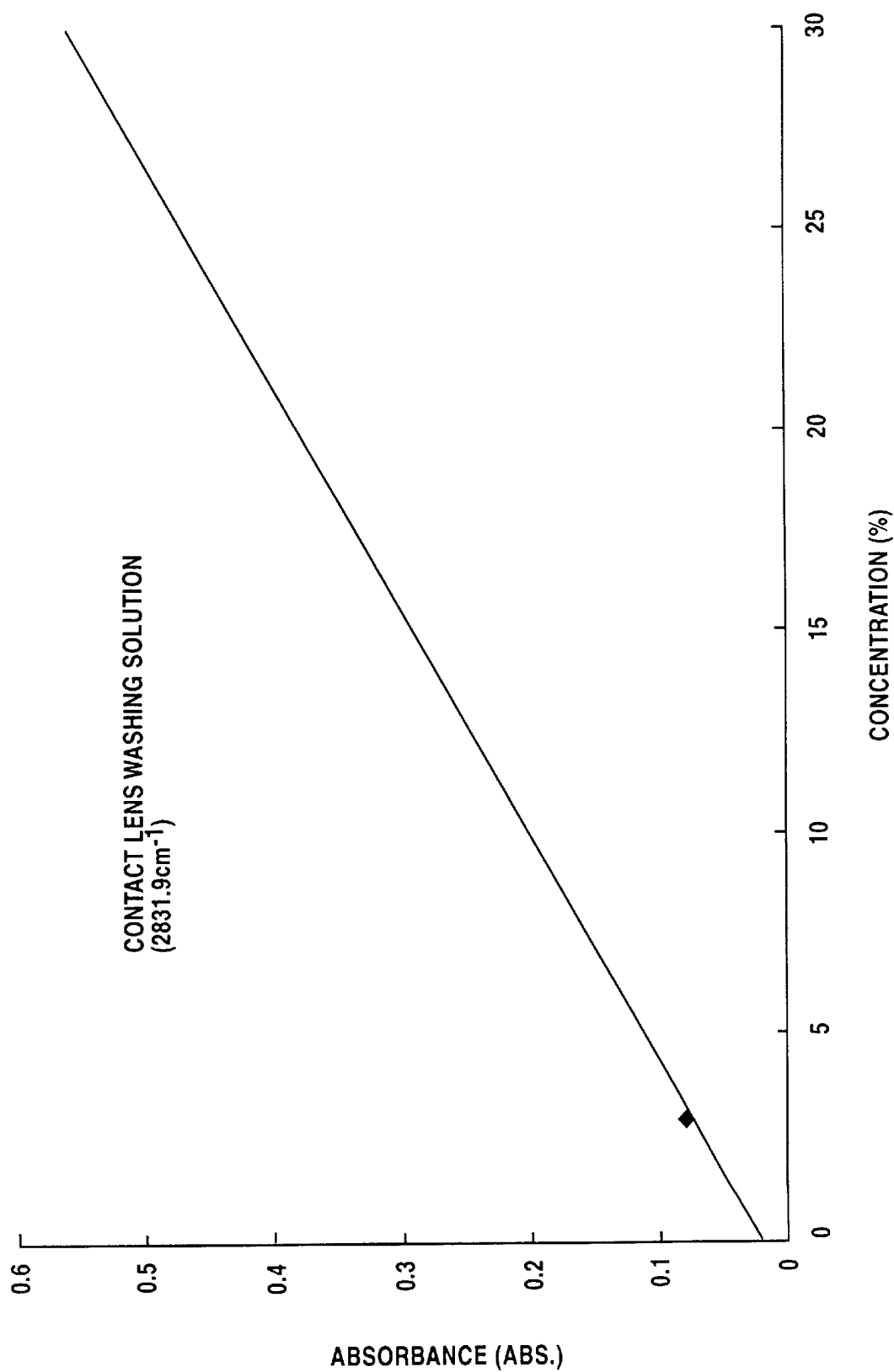
FIG. 10 illustrates the absorbance values at the peak position of 2831.9 cm$^{-1}$ in the total reflection absorption spectra shown in FIG. 8, which are applied to the calibration curve of FIG. 7.

Absorbance of the spectrum at the peak position of 2831.9 $cm^{-1}$ was calculated and applied to the calibration curve of FIG. 7, thereby estimating hydrogen peroxide concentration of 3.18%, as shown in FIG. 10.

Figure 11:
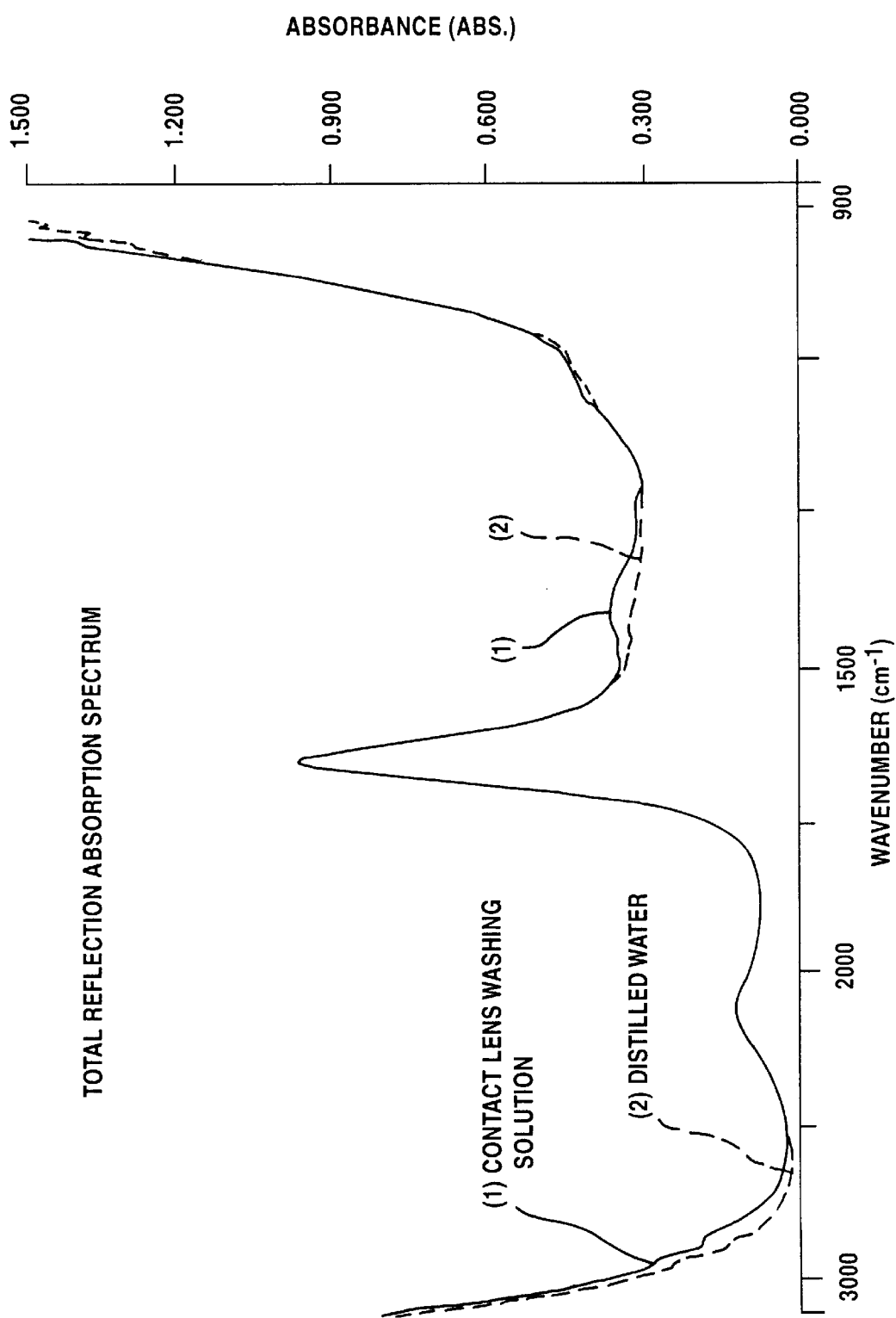
FIG. 11 illustrates total reflection absorption spectra of a commercially available peroxide antiseptic solution and distilled water.

(2) Measurement of Commercially Available Peroxide Antiseptic Solution:

Similarly to the measurement for formation of the calibration curves, a commercially available peroxide antiseptic solution (product by Fujimi Seiyaku Co., Ltd.; indicated as 3 W/V %) was measured to obtain a total reflection absorption spectrum ① shown in FIG. 11. ② shows a total reflection absorption spectrum of distilled water which was measured in a similar manner.

Figure 12:
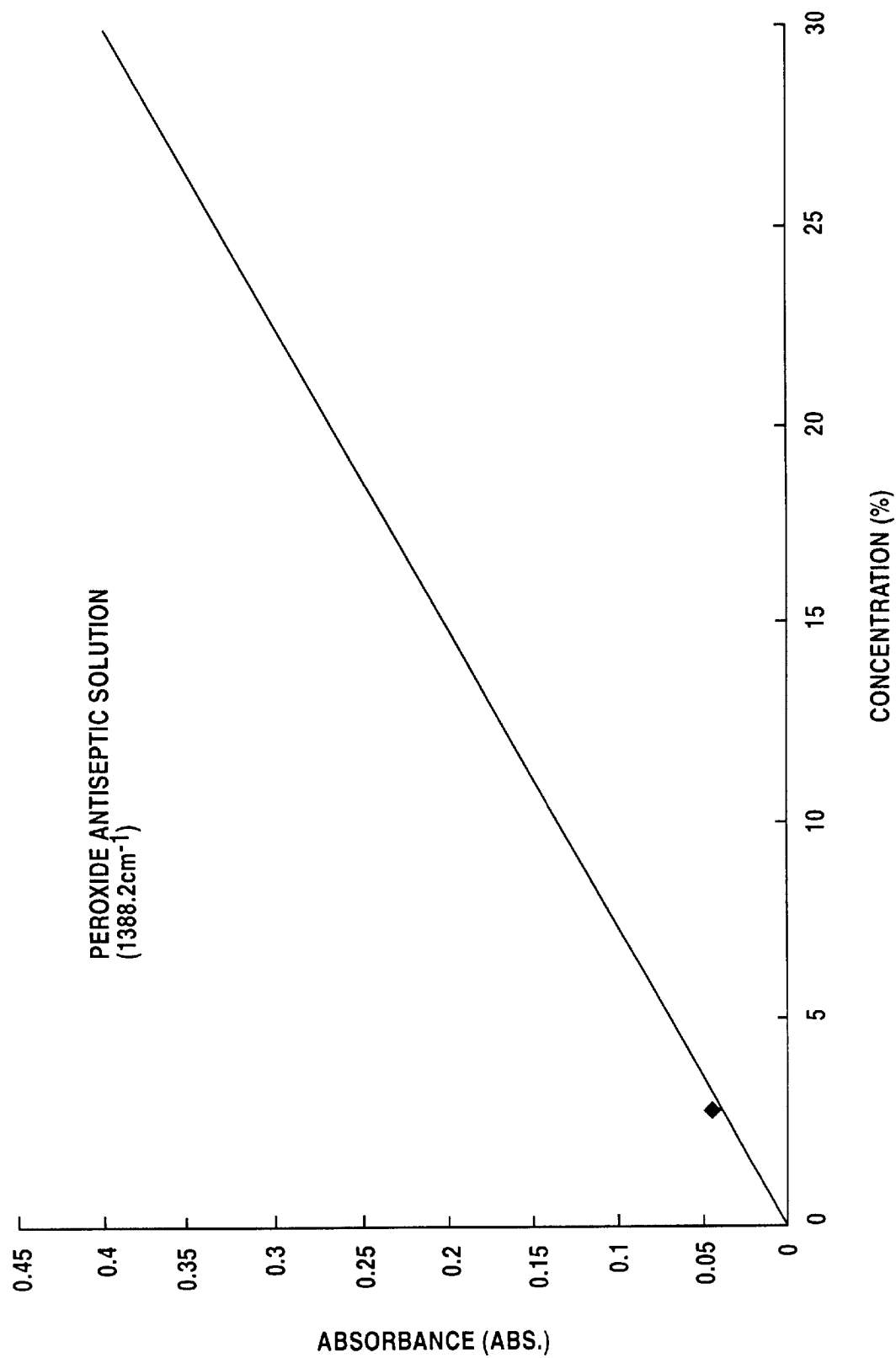
FIG. 12 illustrates the absorbance values at the peak position of 1388.2 cm$^{-1}$ in the total reflection absorption spectra shown in FIG. 11, which are applied to the calibration curve of FIG. 6.

Absorbance of the spectrum at the peak position of 1388.2 $cm^{-1}$ was calculated and applied to the calibration curve of FIG. 6, thereby estimating hydrogen peroxide concentration of 3.26%, as shown in FIG. 12.

Figure 13:
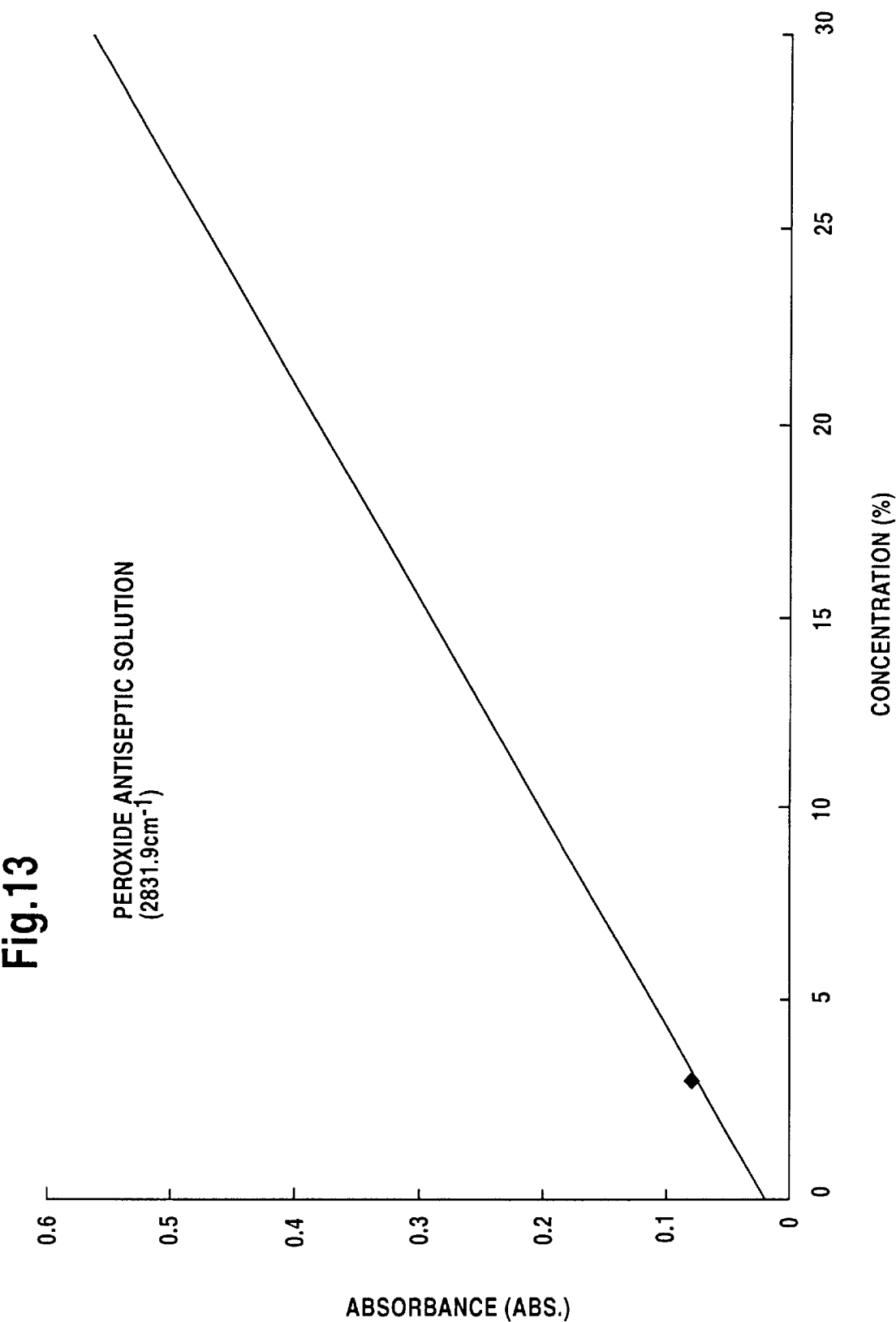
FIG. 13 illustrates the absorbance values at the peak position of 2831.9 cm$^{-1}$ in the total reflection absorption spectra shown in FIG. 11, which are applied to the calibration curve of FIG. 7.

Absorbance of the spectrum at the peak position of 2831.9 $cm^{-1}$ was calculated and applied to the calibration curve of FIG. 7, thereby estimating hydrogen peroxide concentration of 3.32%, as shown in FIG. 13.

Thus, hydrogen peroxide can be determined through absorbance of a total reflection absorption spectrum of a sample solution containing hydrogen peroxide at the peak position of 1388.2 $cm^{-1}$ or 2831.9 $cm^{-1}$.

EXAMPLE 2

Example of making measurement by employing a light-transmittable cell which was made of a quartz crystal, a halogen lamp as a light source and FTIR (Perkin Elmer System 2000) as a spectroscope is now described.

(Formation of Calibration Curve)

Figure 14:
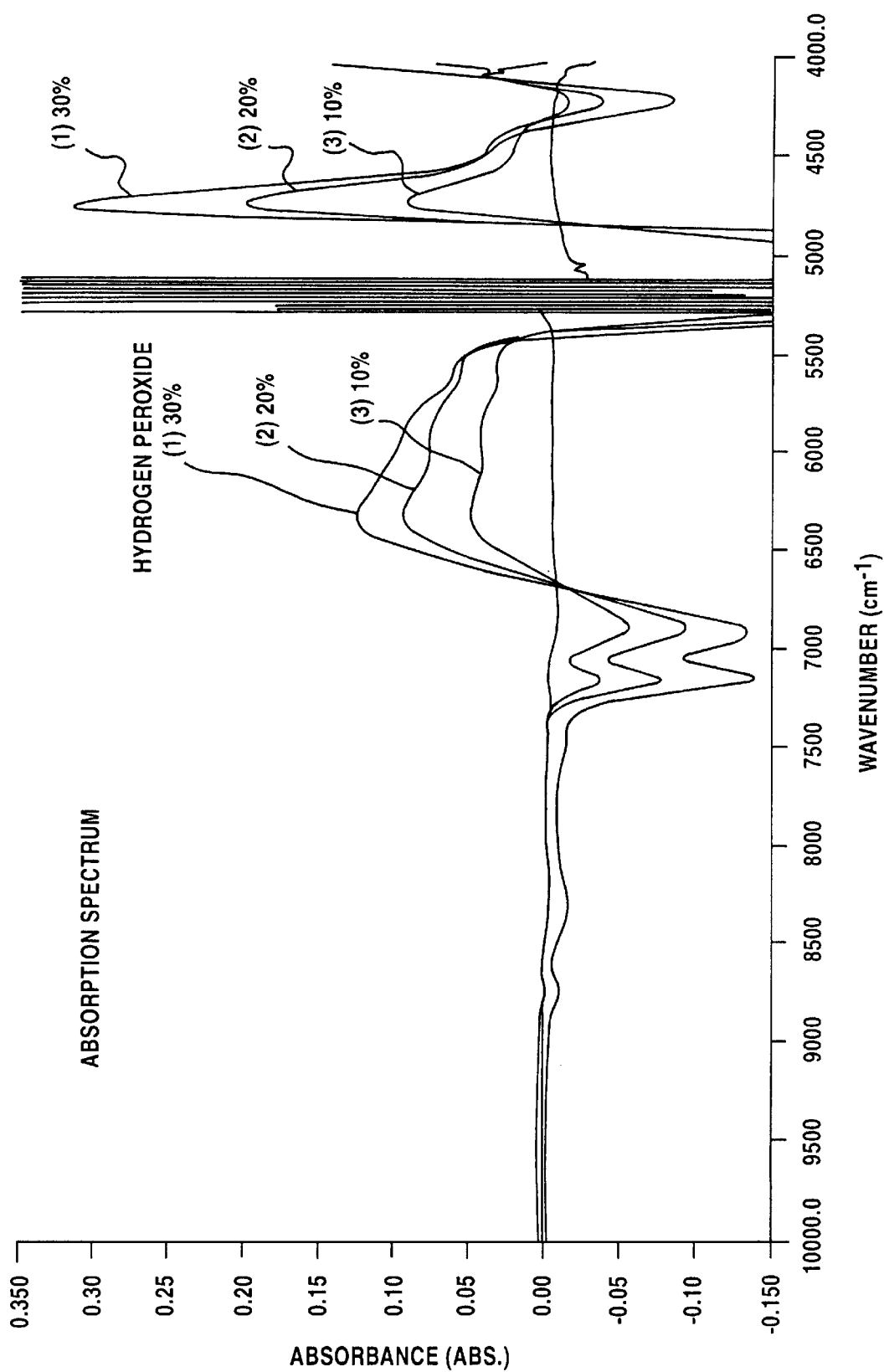
FIG. 14 illustrates near infrared absorption spectra of hydrogen peroxide standard samples of 10 to 30% and distilled water.
Figure 15:
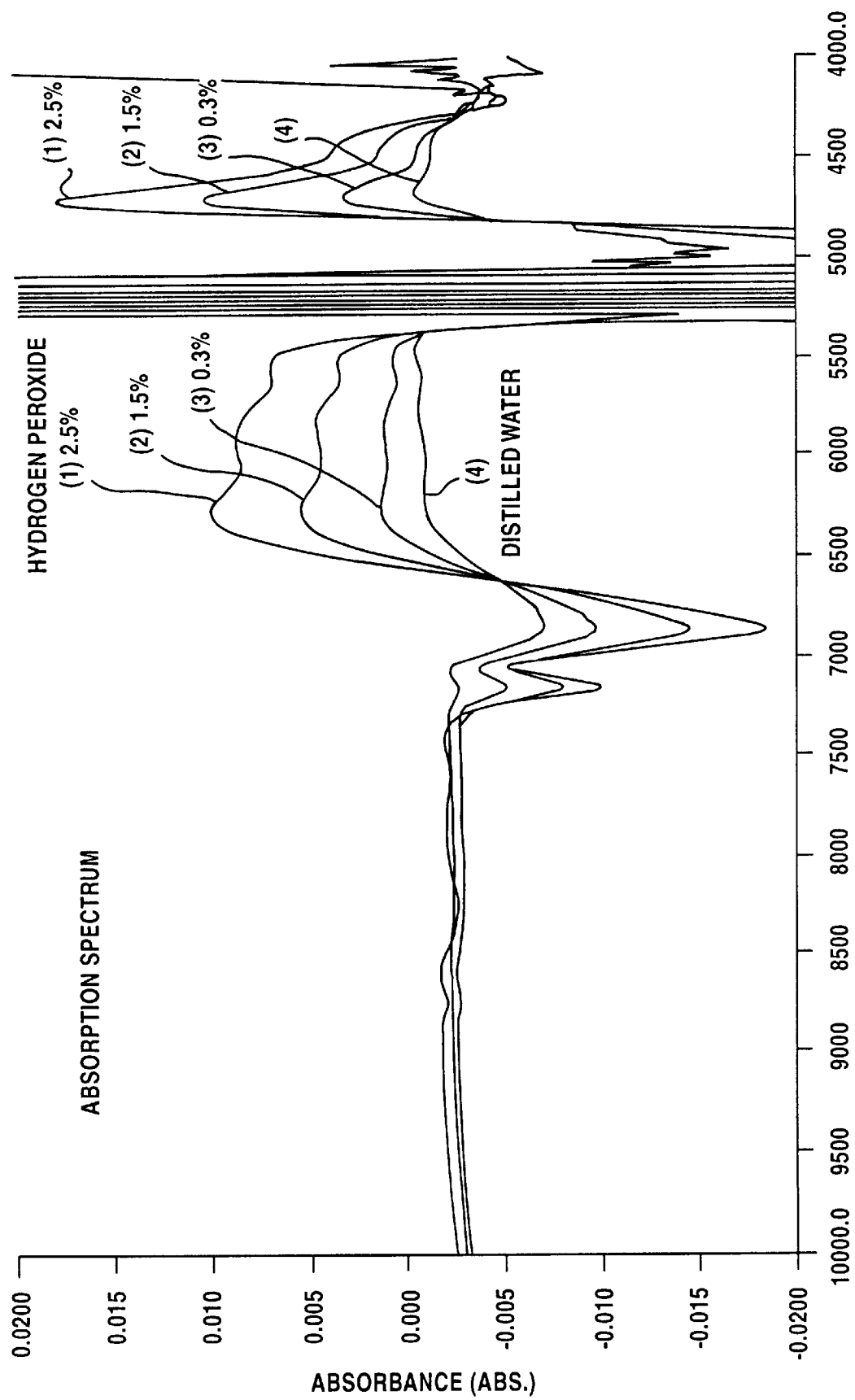
FIG. 15 illustrates near infrared absorption spectra of hydrogen peroxide standard samples of 0.3 to 2.5% and distilled water.
Figure 16:
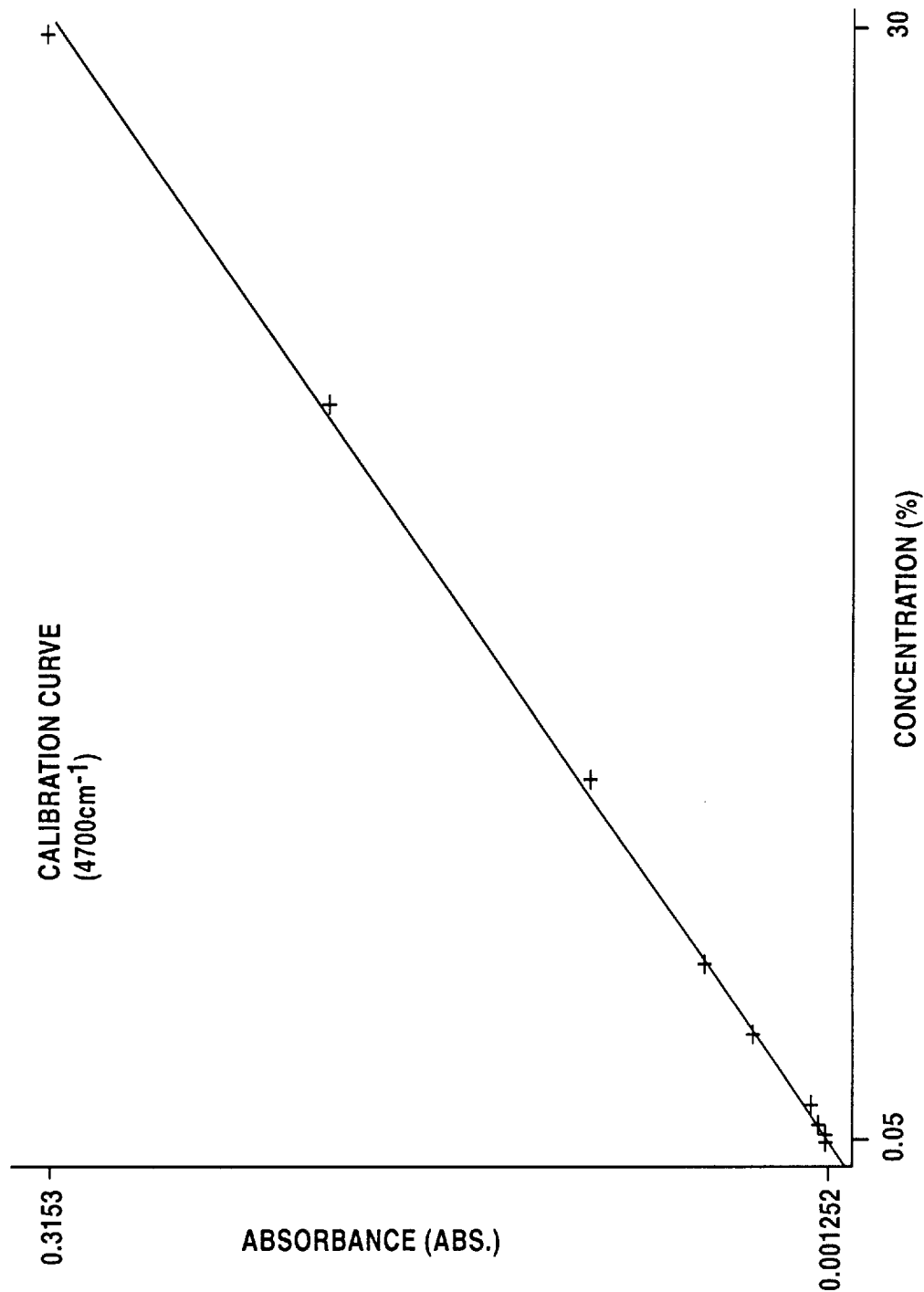
FIG. 16 shows a hydrogen peroxide calibration curve of the absorption spectra shown in FIGS. 14 and 15 at an absorption wavenumber of 4700 cm$^{-1}$.
Figure 17:
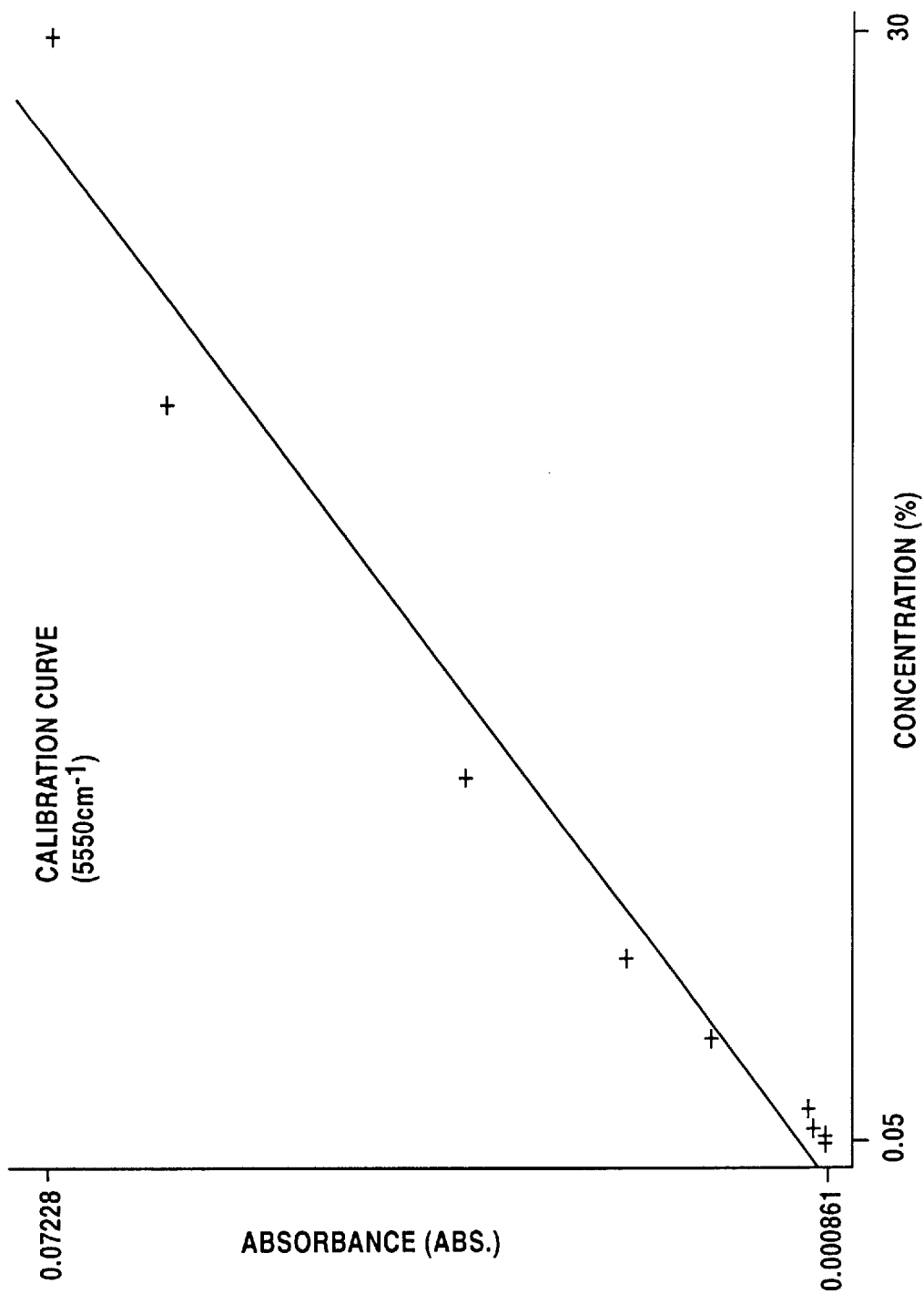
FIG. 17 shows a hydrogen peroxide calibration curve of the absorption spectra shown in FIGS. 14 and 15 at an absorption wavenumber of 5550 cm$^{-1}$.
Figure 18:
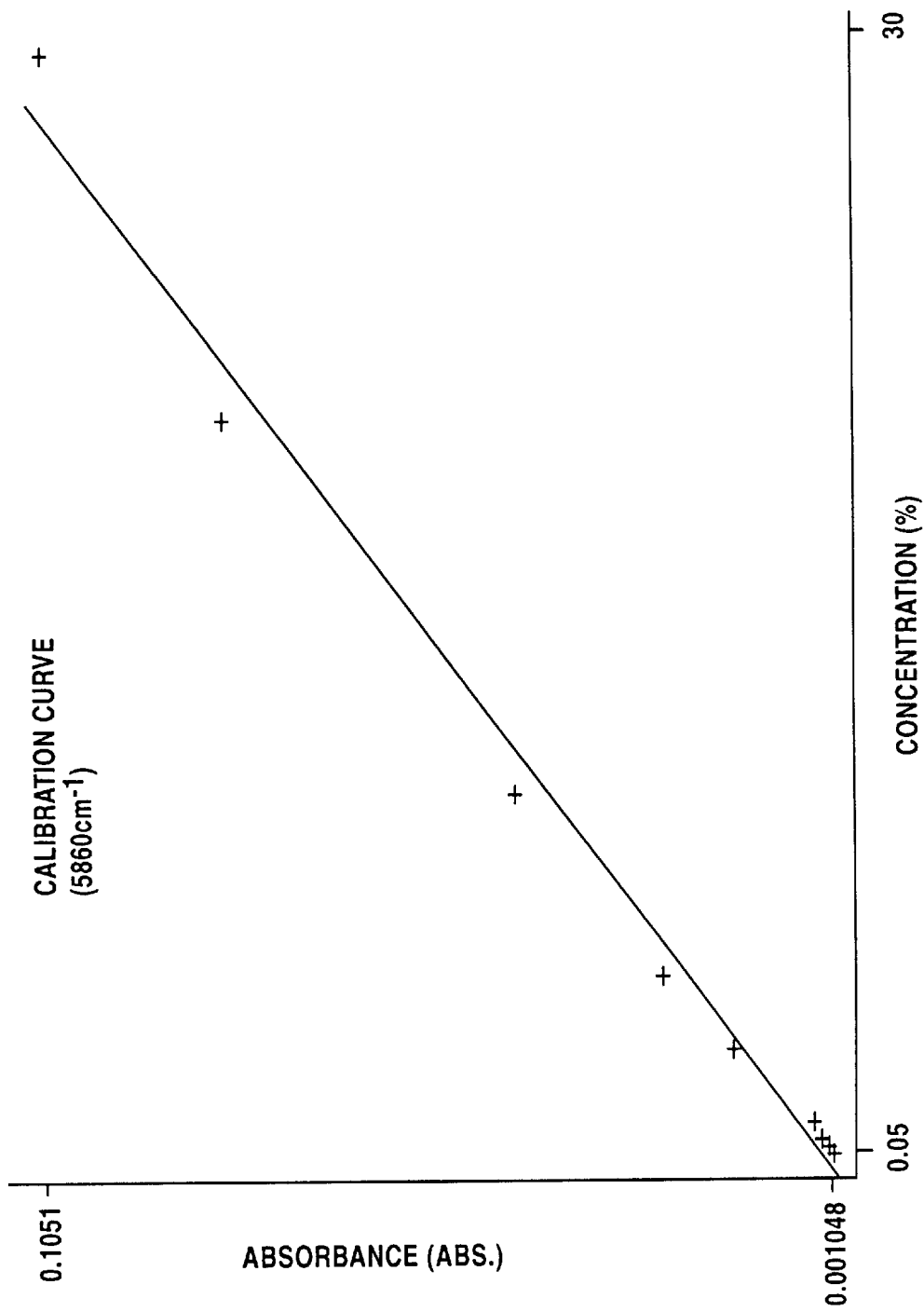
FIG. 18 shows a hydrogen peroxide calibration curve of the absorption spectra shown in FIGS. 14 and 15 at an absorption wavenumber of 5860 cm$^{-1}$.
Figure 19:
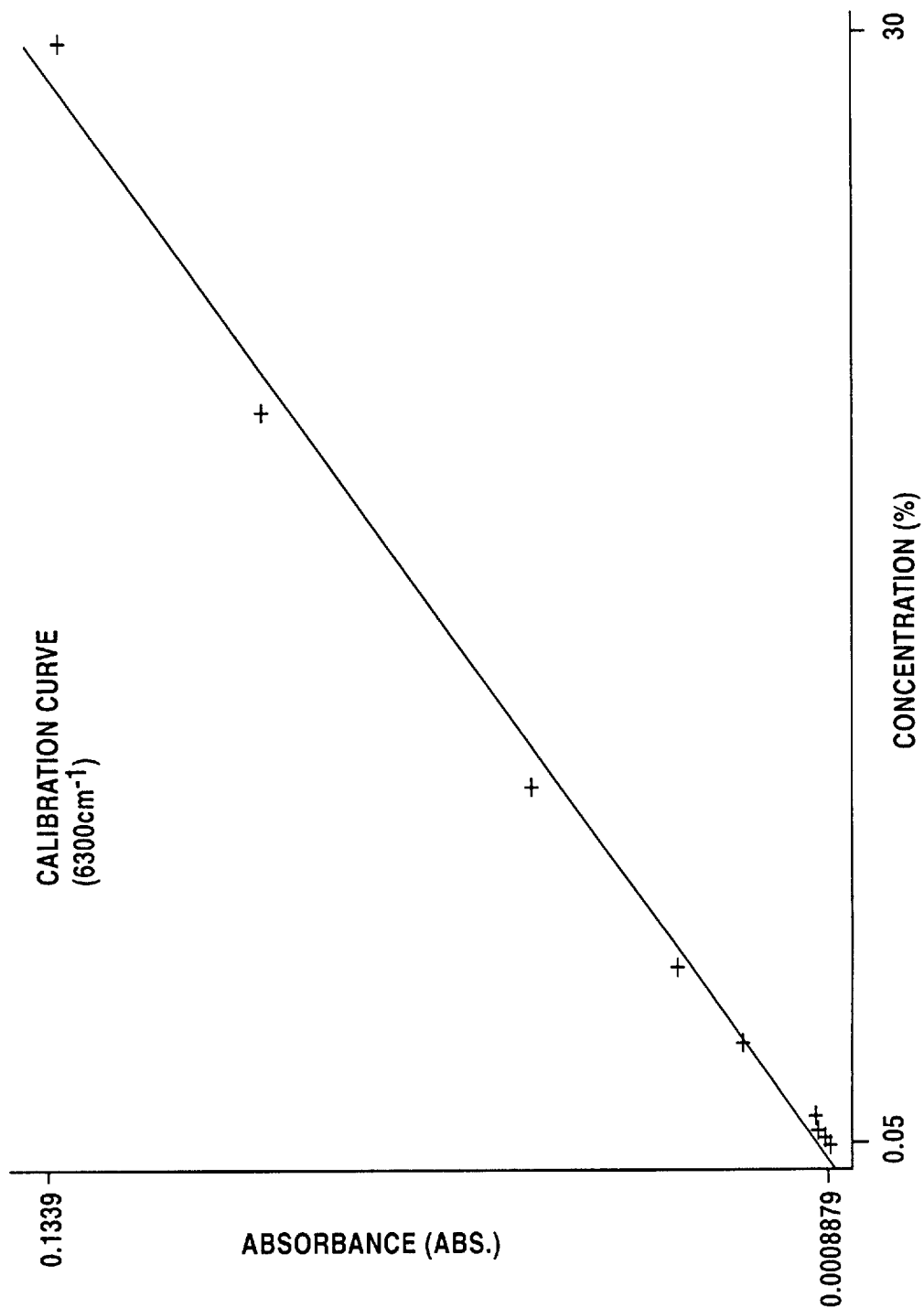
FIG. 19 shows a hydrogen peroxide calibration curve of the absorption spectra shown in FIGS. 14 and 15 at an absorption wavenumber of 6300 cm$^{-1}$.

The same standard hydrogen peroxide reagent of 30% (W/V) as that in Example 1 was diluted with distilled water to prepare hydrogen peroxide standard samples of 30 %, 20%, 10%, 2.5%, 1.5%, 0.75%, 0.3%, 0.225%, 0.15%, 0.075% and 0.03% respectively, and absorption spectra of these standard samples and distilled water were measured. FIGS. 14 and 15 show some of the results in high and low concentration regions respectively. The absorption spectrum of distilled water was subtracted from those of the standard samples in FIG. 14 and 15, and hence absorbance values of the hydrogen peroxide absorption peaks appear on positive sides. The absorption peaks are recognized in the vicinity of 4300 to 4800 $cm^{-1}$, 5500 $cm^{-1}$, 5860 $cm^{-1}$ and 6300 $cm^{-1}$ as characteristic peaks of hydrogen peroxide.

FIGS. 16 to 19 illustrate hydrogen peroxide calibration curves which are formed by plotting absorbance values at peak positions of respective absorption wavenumbers on the axis of ordinates while plotting concentration values on the axis of abscissas and applying straight lines thereto by least square fitting.

(Sample Measurement)

Examples of determining commercially available hydrogen peroxide solutions with these calibration curves are now described.

(1) Measurement of Commercially Available Peroxide Antiseptic Solution:

Similarly to the measurement for formation of the calibration curves, the same commercially available peroxide antiseptic solution as that in Example 1 was measured, to obtain an absorption spectrum shown in FIG. 20. Absorbance values at respective absorption peaks in the vicinity of 4700 $cm^{-1}$, 5500 $cm^{-1}$, 5860 $cm^{-1}$ and 6300 $cm^{-1}$ in this spectrum were obtained and the respective calibration curves shown in FIGS. 16 to 19 were applied to these absorbance values, thereby estimating hydrogen peroxide concentration values of 3.26%, 3.21%, 3.31% and 3.29% respectively.

(2) Measurement of Commercially Available Contact Lens Washing Solution:

Similarly to the measurement for formation of the calibration curves, the same commercially available contact lens washing solution as that in Example 1 was measured, to obtain an absorption spectrum shown in FIG. 21. Absorbance values at respective absorption peaks in the vicinity of 4300 to 4800 $cm^{-1}$, 5500 $cm^{-1}$, 5860 $cm^{-1}$ and 6300 $cm^{-1}$ in this spectrum were obtained and the respective calibration curves shown in FIGS. 16 to 19 were applied to these absorbance values, thereby estimating hydrogen oxide concentration values of 3.12%, 3.22%, 3.18% and 3.08% respectively.

Thus, it is possible to determine hydrogen peroxide through any absorption peak, which is present at 4300 to 4800 cm$^{-1}$ or 5400 to 6600 cm$^{-1}$, of an infrared absorption spectrum of a sample solution containing hydrogen peroxide.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of determining an amount of hydrogen peroxide in an aqueous sample solution, comprising contacting the aqueous sample solution with radiation comprising wavelengths in a region of near infrared to infrared, and determining the amount of hydrogen peroxide in the aqueous sample solution by measuring an absorption of at least one radiation wavelength at a peak position of an absorption spectrum which is specific to hydrogen peroxide, and comparing the measured absorption to a calibration curve which indicates a relation between the amount of hydrogen peroxide and the measured absorption at the peak position.

2. The method in accordance with claim 1, wherein the aqueous sample solution is an aqueous sample solution which already contains hydrogen peroxide.

3. The method in accordance with claim 1, wherein the aqueous sample solution is a reactive solution which has been so prepared as to enable an enzyme to mediate an enzyme reaction which generates the amount of hydrogen peroxide.

4. The method in accordance with claim 3, wherein the enzyme reaction is represented by the formula:

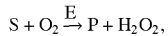

wherein S represents a quantity of substrate, P represents a quantity of product and E represents the enzyme.

5. The method in accordance with claim 4, wherein the quantity of the substrate S or the product P is determined as a function of the determined amount of hydrogen peroxide.

6. The method in accordance with claim 4, wherein the substrate and the enzyme are selected from combination groups consisting of glucose and glucose oxidase, cholesterol and cholesterol oxidase, urate and uricase and pyruvic acid and pyruvate oxidase.

7. The method in accordance with claim 3, wherein the enzyme has an enzyme activity which is determined as a function of the determined amount of generated hydrogen peroxide.

8. The method in accordance with claim 3, wherein the enzyme is an oxidase.

9. The method in accordance with claim 1, wherein the aqueous sample solution is a reactive solution which has been prepared so as to cause an enzyme to mediate an enzyme reaction which decomposes hydrogen peroxide.

10. The method in accordance with claim 9, wherein the enzyme reaction is represented by the formula:

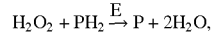

wherein PH$_2$ represents a quantity of reactant, P represents a quantity of product and E represents the enzyme.

11. The method in accordance with claim 10, wherein the quantity of the reactant PH$_2$ or the product P is determined as a function of the determined amount of hydrogen peroxide remaining after the enzyme reaction.

12. The method in accordance with claim 10, wherein the enzyme E is a dehydrogenase selected from the group consisting of peroxidase and catalase.

13. The method in accordance with claim 1, wherein the aqueous sample solution is a reaction system containing a quantity of reactant labelled with a compound which is reactive with hydrogen peroxide, and the method further comprises, before said contacting step, reducing a predetermined quantity of hydrogen peroxide by reacting the predetermined quantity of hydrogen peroxide with the reactant to obtain a lesser amount of hydrogen peroxide, and wherein the quantity of reactant is determined as a function of the lesser amount of hydrogen peroxide obtained.

14. The method in accordance with claim 13, wherein the reactant is an anti-antibody, the compound is peroxidase, and the method further comprises, before said reducing step, reacting the peroxidase-labelled anti-antibody with an antigen-antibody reaction combination to produce a reaction product, performing BF separation to separate any unreacted labelled anti-antibody from the reaction product, and thereafter performing said reducing step with the reaction product.

15. A method of determining an amount of hydrogen peroxide in an aqueous sample solution, comprising disposing the aqueous sample solution in a measuring cell having a total reflection prism on at least one surface thereof, contacting the aqueous sample solution with radiation comprising wavelengths in a region of near infrared to infrared by introducing the radiation into the total reflection prism to contact an interface between an internal surface of the total reflection prism and the aqueous sample solution, and determining the amount of hydrogen peroxide in the sample solution by measuring an absorption of radiation of any absorption band that is present at at least one of 1200 to 1500 cm$^{-1}$ and 2600 to 3000 cm$^{-1}$ in radiation being transmitted through the total reflection prism.

16. A method of determining an amount of hydrogen peroxide in an aqueous sample solution, comprising disposing the aqueous sample solution in a light-transmittable cell, contacting the aqueous sample solution with radiation comprising wavelengths in a region of near infrared, and determining the amount of hydrogen peroxide in the aqueous sample solution by measuring an absorption of radiation of any absorption band that is present at at least one of 4300 to 4800 cm$^{-1}$ and 5400 to 6600 cm$^{-1}$ in radiation being transmitted through the aqueous sample solution.

17. A hydrogen peroxide determination apparatus, comprising:

a total reflection cell having wall surfaces, at least one of the wall surfaces defining a space for receiving an aqueous sample solution having a first refractive index, and comprising a total reflection prism made of a material having a second refractive index which is larger than the first refractive index;

an incident optical system for introducing a measuring beam of radiation into the total reflection prism at an angle of incidence for causing total reflection;

a measuring optical system for receiving an outgoing beam of radiation from the total reflection prism;

means for measuring an absorption of at least one absorption band which is specific to hydrogen peroxide in the outgoing beam at at least one of 1200 to 1500 cm$^{-1}$ and 2600 to 3000 cm$^{-1}$; and means for determining an amount of hydrogen peroxide using the measured absorption.

18. The hydrogen peroxide determination apparatus in accordance with claim 17, wherein the total reflection cell is a flow cell, having a sample solution inlet port and a sample solution outlet port, and means to feed the aqueous sample solution to the cell.

19. The hydrogen peroxide determination apparatus in accordance with claim 17, wherein the total reflection cell is a cell having only one opening.

* * * * *